(12) United States Patent
Patel

(10) Patent No.: US 11,877,805 B2
(45) Date of Patent: Jan. 23, 2024

(54) TRAJECTORY PLANNING FOR A MEDICAL ROBOT SYSTEM

(71) Applicant: Siemens Healthcare GmbH, Erlangen (DE)

(72) Inventor: Ankit Patel, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 18/110,071

(22) Filed: Feb. 15, 2023

(65) Prior Publication Data

US 2023/0270501 A1 Aug. 31, 2023

(30) Foreign Application Priority Data

Feb. 25, 2022 (DE) ...................... 10 2022 201 952.0

(51) Int. Cl.
*A61B 34/10* (2016.01)
*A61B 34/30* (2016.01)
*A61B 6/00* (2006.01)

(52) U.S. Cl.
CPC ............ *A61B 34/10* (2016.02); *A61B 6/4441* (2013.01); *A61B 6/547* (2013.01); *A61B 34/30* (2016.02); *A61B 2034/107* (2016.02)

(58) Field of Classification Search
CPC ....... A61B 34/10; A61B 6/4441; A61B 6/547; A61B 34/30; A61B 2034/107
See application file for complete search history.

(56) References Cited

U.S. PATENT DOCUMENTS

| 9,398,675 B2 * | 7/2016 | Eaves ................... A61B 6/4441 |
| 2009/0274271 A1 * | 11/2009 | Pfister .................. A61B 6/5229 378/65 |
| 2018/0008217 A1 * | 1/2018 | Gemmel .............. A61B 6/4441 |

FOREIGN PATENT DOCUMENTS

| DE | 10153787 B4 | 4/2005 |
| DE | 102012200686 A1 | 1/2013 |
| EP | 3693137 A1 | 8/2020 |

* cited by examiner

*Primary Examiner* — Rachid Bendidi
(74) *Attorney, Agent, or Firm* — Lempia Summerfield Katz LLC

(57) ABSTRACT

A method of trajectory planning for a medical robot system is disclosed herein, wherein a pose of a first component of the robot system may be changed independently of a pose of a second component of the robot system. The method includes determining an initial status, wherein, for each degree of freedom, an initial value is measured. Based on the initial status, items of position information of at least two discrete reference points of the first component in respect of one another are determined as well as further items of position information of at least two discrete further reference points of the second component in respect of one another. Depending on the initial status, the items of position information and the further items of position information, a trajectory for the robot system is planned, which transfers the robot system from the initial status into a target status.

6 Claims, 7 Drawing Sheets

TRAJECTORY PLANNING FOR A MEDICAL ROBOT SYSTEM

The present patent document claims the benefit of German Patent Application No. 10 2022 201 952.0, filed Feb. 25, 2022, which is hereby incorporated by reference in its entirety.

TECHNICAL FIELD

The present disclosure relates to a method of trajectory planning for a medical robot system having a large number of degrees of freedom, wherein a pose of a first component of the robot system may be changed independently of a pose of a second component of the robot system and wherein an initial status of the robot system is determined in that for each of the degrees of freedom, an initial value is obtained. The disclosure also relates to a robotic apparatus having a medical robot system having a large number of degrees of freedom, the robot system having an actuator system having a large number of actuators, wherein the actuator system is configured to change a pose of a first component of the robot system independently of a pose of a second component of the robot system, and a measuring system, which is configured to measure an initial value for each of the degrees of freedom. The disclosure also relates to an apparatus for data processing and to a computer program.

BACKGROUND

In medical robot systems having a plurality of independent components, for example, an imaging system and a patient couch, very complex positions of the components relative to one another may result, which may make access to the patient difficult or impossible. This is disadvantageous in particular in critical situations if, for instance, a heart-lung resuscitation of the patient by medical staff is necessary.

Conventional methods for trajectory planning calculate the distances of critical surfaces of the robot system relative to one another and then proceed iteratively. That is to say, the status of the robot system is easily changed, the changed distances are calculated again and compared with specified limit values. If one of the distances undershoots the corresponding limit value, the change in the status is thus discarded and another change in the status assumed. If the limit values are observed, the process continues starting from the changed status. This is repeated until an acceptable end status is attained.

These methods have the drawback that, owing to their iterative character, they require quite a lot of time until the trajectory is planned. Furthermore, the movement cannot be predicted, or may only be predicted with difficulty, by medical staff. This may also apply to the end status. In addition, the computing effort for trajectory planning is also very high because the distances of whole surfaces relative to one another have to be calculated multiple times. In addition, an exact surface model is necessary for the robot system.

From document EP 3 693 137 A1, a method is known for producing a path planning module and for operating a robot. The path planning module has an AI component, which is trained on the basis of specified input data and a training target specification to distinguish unsafe movements of the robot from safe movements and to determine a respective path from an initial pose of the robot to a respective target.

From document DE 101 53 787 B4, an X-ray diagnosis facility is known, having a multiply motor-adjustable mount arranged on an equipment cart, on which mount a C-arm with an X-ray beam source and an X-ray beam receiver arranged opposite it is mounted so as to be manually displaceable along its circumference. The mount has components or devices for determining the relative position of the C-arm in respect of the mount. An axis controller controls the motor-driven adjustment of the mount synchronously with the manual movement of the C-arm in the mount in such a way that for a target within an examination object, a predetermined condition is met for the X-ray mapping geometry.

From document DE 10 2012 200 686 A1, a method for positioning an X-ray apparatus relative to an imaging apparatus is known. The method includes: (S1) with the aid of an imaging apparatus, acquisition of an image dataset in a reference coordinate system particular to the imaging apparatus; (S2) obtaining coordinates within the image dataset and determining first items of positioning data for the X-ray apparatus in such a way that a radiograph with the X-ray apparatus, which takes into account the first items of positioning data, includes image information at the coordinates, which correspond to the coordinates within the image dataset; (S3) transferring the first items of positioning data to the X-ray apparatus; (S4) determining the position of the examination region in a reference coordinate system particular to the X-ray apparatus and determining second items of positioning data as a function of a transformation of the reference coordinate system, particular to the imaging apparatus, in that of the X-ray apparatus; and (S5) positioning the X-ray apparatus as a function of the second items of positioning data.

SUMMARY AND DESCRIPTION

It is an object of the present disclosure to improve the trajectory planning for a medical robot system having a large number of degrees of freedom, which has two or more components that may move independently of one another in order to reduce, in particular, the planning time and/or the computing effort and/or the requirements of a model of the robot system that is to be provided.

The scope of the present disclosure is defined solely by the appended claims and is not affected to any degree by the statements within this summary. The present embodiments may obviate one or more of the drawbacks or limitations in the related art.

The disclosure relates to basing the trajectory planning on items of position information of discrete reference points to the components of the robot system.

According to one aspect, a method of trajectory planning for a medical robot system having a large number of degrees of freedom is disclosed. The robot system has a first component and a second component, wherein a pose of the first component may be changed independently of a pose of the second component, for example, by a large number of actuators of the robot system. An initial status of the robot system is determined in that for each of the degrees of freedom of the large number of degrees of freedom, an initial value is obtained, (e.g., measured), in particular from or by a measuring system of the robot system. On the basis of the initial status, items of position information of at least two, in particular specified, discrete reference points of the first component in respect of one another are determined, in particular by at least one computing unit. On the basis of the initial status, further items of position information of at least two, in particular specified, discrete further reference points of the second component in respect of one another are determined, in particular by the at least one computing unit. Depending on the initial status, the items of position information and the further items of position information, a trajectory is planned for the robot system, in particular by the at least one computing unit, which transfers the robot system from the initial status into a target status, in particular a specified target status, of the robot system.

The robot system and the at least one computing unit may be component parts of a robotic apparatus. A robot system may refer to a system including one or more robot(s). A robot may be comprehended as an apparatus, which has one or more moving part(s), which are freely movable in respect of two or more, (e.g., three or more), axes of movement, with the movement taking place automatically, for example, on the basis of corresponding programming, and possibly being limited by mechanical, dynamic, or other restrictions. The axes of movement may include linear axes of movement and/or axes of rotation. Each axis may be comprehended as a degree of freedom.

A medical robot system may refer to a robot system configured to carry out a medical application. It may be systems for medical imaging, for example, X-ray-based imaging, and/or for carrying out or assisting medical interventions. For example, computed tomography systems or angiography systems, in particular systems for interventional angiography, may be configured as medical robot systems.

The medical robot system, whose trajectory is planned, has a large number of degrees of freedom, three or more degrees of freedom of axes of movement, therefore. At least one first degree of freedom of the large number of degrees of freedom relates to the first component, and at least one second degree of freedom of the large number of degrees of freedom to the second component. The entirety of the at least one first degree of freedom determines the pose of the first component and the entirety of the at least one second degree of freedom determines the pose of the second component. The pose may refer to the entirety of three corresponding spatial coordinates, translational positions therefore, and three corresponding orientation angles, rotatory positions, therefore. It is not necessarily possible to change all six translational and rotatory positions of the component independently or interdependently, however. For example, individual translational positions and/or rotatory positions may be defined by the configuration of the respective component or by other boundary conditions. The pose of one of the components may also be referred to as the status of the respective component, the poses of the first and the second components together as the status of the robot system.

The first component and the second component may belong to two different robots of the robot system, for instance a robot stand, also referred to as a robot support, and a robotic patient couch, also referred to as a patient table. The first component and the second component may also be part of the same robot, however. In both cases, the pose of the first component may be changed independently of the pose of the second component. In other words, the pose of the first component may be changed in a given reference coordinate system and the pose of the second component may remain unchanged in the same reference coordinate system, or vice versa. This does not rule out a simultaneous change in the poses of the first component and the second component, however.

The robot system may have an actuator system that contains the large number of actuators, (e.g., motors), and a corresponding control system for controlling the actuators. The poses of the first and second components may be changed independently of one another by appropriate control of the large number of actuators.

The value, which is measured for each of the degrees of freedom, corresponds, (e.g., directly or indirectly), to the respective translational or rotatory position, which corresponds to the degree of freedom. The position is measured directly or may be derived from the measured value. The measuring system may contain corresponding sensors, for example, rotary encoder and the like, for measuring the position, for example, by way of an appropriate measurement of an actuator position or setting.

The reference points are defined, in particular, in advance. In other words, there is a known, specified, clear correlation between the at least one first degree of freedom and the coordinates of the at least two reference points. Analogously, there is a known, specified, clear correlation between the at least one second degree of freedom and the coordinates of the at least two further reference points.

The at least two reference points do not necessarily lie on a surface of the first component but are defined in respect of the first component, as stated above. At least one reference point of the at least two reference points may have a distance from the first component greater than zero, and therefore does not lie on any surface of the first component. This has the advantage that particularly relevant reference points, for example, points of symmetry or potential collision points, may be used for trajectory planning. The at least two further reference points do not necessarily lie on a surface of the second component but are defined in respect of the second component, as stated above. At least one reference point of the at least two further reference points may have a distance from the second component greater than zero, and therefore not lie on any surface of the second component.

The reference points being discrete may refer to distinct points from continuous points. A surface in the space is given, for example, by a quantity of continuous points, each point has an infinite quantity of adjacent points, therefore, from which it has no distance. There is a finite distance between two discrete points, by contrast. In the case of the at least two discrete reference points and the at least two further discrete reference points, it is possible to define, in particular, a minimum distance, so any pair of points of the at least two reference points has a distance from one another, which is greater than or equal to the minimum distance, and any pair of points of the at least two further reference points has a distance from one another, which is greater than or equal to the minimum distance. The minimum distance for the at least two reference points may also differ from that for the at least two further reference points, however. The respective minimum distance may be in the order of magnitude of a few centimeters or more, for example, greater than or equal to 5 cm or greater than or equal 10 cm, or lie in the range of 5 cm to 50 cm or in the range of 10 cm to 50 cm.

The items of position information of the at least two reference points may include the respective three-dimensional coordinates of the at least two reference points. Consequently, the position of the at least two reference points relative to one another is also defined. Alternatively, the items of position information may include only the position of the at least two reference points relative to one another. Combinations are also possible. The same applies analogously to the further items of position information of the at least two further reference points.

The trajectory of the robot system may refer to the trajectory in the multi-dimensional space, at least three-dimensional space, which is spanned by the entirety of the large number of degrees of freedom, therefore. Each status of the robot system is given by exactly one point in the multi-dimensional space. The trajectory is a curve or hyper-curve in the multi-dimensional space, therefore, which leads from the initial status to the target status, transfers the robot system from the initial status into the target status therefore, if the actuators are actuated accordingly.

The target status of the robot system may be calculated dependent, for example, on the initial status, the items of position information, and/or the further items of position information, in particular by the at least one computing unit. Alternatively, the target status may follow from the trajectory planning. Alternatively, the target status may be specified. Combinations of these alternatives are also possible. For example, a target range may be specified for the target status and the exact target status may be calculated from the trajectory planning or as explained.

By using the discrete reference points for trajectory planning, in particular distinct from approaches, which are based on the calculation of distances between surfaces, it is possible to simplify, and therewith accelerate, trajectory planning. In particular, by way of suitable, system-specific, selection of the reference points a limitation to the actually relevant geometric properties of the robot system is possible without a comprehensive model, in particular surface model, being required. Consequently, in particular, a trajectory planning may be implemented in which the trajectory from the initial status through to the target status is planned without iterative intermediate acts being required for collision testing, without it being necessary to check for intermediate states between the initial status through to the target status, whether a collision of the components with one another or possibly one of the components with a patient is probable.

The method of trajectory planning disclosed herein does not include actuation of the actuators in order to actually transfer the robot system from the initial status into the target status, and therefore does not include the transfer itself. From each implementation of the method of trajectory planning, a corresponding method for controlling the medical robot system follows, however, in accordance with which the robot system is transferred along a planned trajectory from an initial status of the robot system into a target status of the robot system, with a method of trajectory planning being carried out in order to plan the trajectory for the robot system.

Furthermore, the method of trajectory planning may refer to a combination of a computer-implemented method of trajectory planning with the preceding act of measuring the initial values. Each act of the computer-implemented method may be carried out by an apparatus for data processing, in particular at least one processor of the apparatus for data processing. The apparatus for data processing may be the at least one computing unit or contain the at least one computing unit.

According to at least one embodiment of the method of trajectory planning, the robot system contains a medical imaging modality having the first component and a patient couch having the second component.

The patient couch, in particular a supporting plate of the patient couch, may be rotated or tilted or inclined, for example, about one, two, or three axes. Furthermore, the entire patient couch as a whole or the supporting plate in respect of a support component of the patient couch may be translationally moved, for example, in one, two, or three direction(s).

The imaging modality may be configured, for example, as a C-arm system, also as a C-arm system, for medical imaging, for example, for X-ray-based imaging, in particular computed tomography, and/or X-ray-based angiography, and/or for interventional angiography. The C-arm system may be configured, for example, as a C-arm system mounted on the ceiling or as a mobile C-arm system.

Robot systems with C-arm system and patient couches as described have a high number of degrees of freedom, for example, three rotatory degrees of freedom of the C-arm system, and one, two, or three rotatory degrees of freedom of the patient couch, and possibly additional translational degrees of freedom. Accordingly, the states of the robot system may be highly complex, whereby highly complex poses of the first and second components relative to one another may result. The advantages of the disclosure are particularly effective here, therefore.

According to at least one embodiment, the first component corresponds to a C-arm for X-ray-based imaging, or the imaging modality has the C-arm and the first component is rigidly attached to the C-arm.

For example, an X-ray detector and/or an X-ray collimator may be attached to the C-arm.

According to at least one embodiment, a first reference point of the at least two reference points corresponds to a center of the C-arm and a second reference point of the at least two reference points lies on an, in particular straight, line, which connects an X-ray detector of the C-arm to an X-ray collimator of the C-arm and runs through the center of the C-arm.

In other words, the first reference point is in any case located between the X-ray detector and the X-ray collimator. The second reference point may lie in or on the X-ray detector or X-ray collimator.

According to the disclosure, the trajectory for the robot system is planned dependent on a first reference vector, which points from the first reference point to the second reference point.

It has been found that the items of position information of these reference points relative to one another, in particular their relative position to one another, which is given by the first reference vector, are paramount for the C-arm-systems and may therefore advantageously be used for comprehensive trajectory planning. Owing to the movement possibilities of a C-arm system, this first reference vector may be sufficient to form the items of position information. In other words, the items of position information may include the first reference vector. By taking into account the further items of position information, it is then possible to carry out the trajectory planning efficiently and reliably.

A second reference vector, which is perpendicular to the supporting plate of the patient couch, is calculated dependent on the initial status. An alignment of the first reference vector is controlled or regulated in respect of the second reference vector for planning the trajectory.

A third reference vector, which is parallel to the supporting plate of the patient couch, is calculated dependent on the initial status. An alignment of the first reference vector is controlled or regulated in respect of the third reference vector for planning the trajectory.

The second and/or the third reference vector(s) may be regarded, in particular, as part of the further items of position information, therefore. The second and/or the third reference vector(s) may be calculated, in particular, dependent on the initial status and the at least two second reference points.

The planning of the trajectory is carried out in such a way that a first angle between the second reference vector and a projection of the first reference vector is minimized in a plane perpendicular to the third reference vector, or the planning of the trajectory is carried out in such a way that a second angle between the third reference vector and a projection of the first reference vector is minimized in a plane perpendicular to the second reference vector.

In particular, the trajectory is planned in such a way that the first angle and/or the second angle are as small as possible throughout the entire trajectory. For this, one or more optimization method(s), (e.g., with specified boundary conditions), may be carried out.

According to at least one embodiment, the C-arm is mounted and/or guided in such a way that the C-arm may be orbitally rotated about a first axis of rotation and about a second axis of rotation, which is perpendicular to the first axis of rotation, with the orbital rotation about the first axis of rotation and the rotation about the second axis of rotation corresponding to mutually independent degrees of freedom of the large number of degrees of freedom.

The orbital rotation may be comprehended, in particular, as a rotation of the C-arm within the plane defined by the C-arm. Substantially any cranial or caudal settings of the C-arm and substantially any LAO/RAO settings of the C-arm may accordingly be achieved by the orbital rotation about the first axis of rotation and the rotation about the second axis of rotation. LAO and RAO stand for left anterior oblique and right anterior oblique respectively.

According to at least one embodiment, the trajectory is planned in such a way that a respective distance between the first reference point and each further reference point of the at least two further reference points is continuously enlarged and/or remains constant when the robot system transfers along the trajectory from the initial status into the target status. In other words, the respective distance between the first reference point and each further reference point is not reduced at any instant when the robot system transfers along the trajectory from the initial status into the target status.

A collision of the components with one another and/or a collision of one of the components with a patient may consequently be avoided.

According to at least one embodiment, the trajectory is planned in such a way that a respective distance between the second reference point and each further reference point of the at least two further reference points is continuously enlarged and/or remains constant when the robot system transfers along the trajectory from the initial status into the target status. In other words, the respective distance between the second reference point and each further reference point is not reduced at any instant when the robot system transfers along the trajectory from the initial status into the target status.

According to a further aspect, an apparatus for data processing is disclosed. The apparatus has at least one processor configured to carry out a computer-implemented method as disclosed herein. According to the computer-implemented method, an initial status of a medical robot system is obtained, wherein a pose of a first component of the robot system may be changed independently of a pose of a second component of the robot system, in the form of measured initial values for each degree of freedom of a large number of degrees of freedom of the robot system, in particular from a measuring system of the robot system. Items of position information of at least two discrete reference points of the first component are determined in respect of one another on the basis of the initial status. Further items of position information of at least two discrete further reference points of the second component are determined in respect of one another on the basis of the initial status. A trajectory is planned for the robot system, which transfers the robot system from the initial status into a target status of the robot system, dependent on the initial status, the items of position information and the further items of position information.

Further designs of the apparatus for data processing follow directly from the different embodiments of the method of trajectory planning, and vice versa.

According to a further aspect, a robotic apparatus is disclosed. The robotic apparatus has a medical robot system having a large number of degrees of freedom. The robot system has an actuator system having a large number of actuators, wherein the actuator system is configured to change a pose of a first component of the robot system independently of a pose of a second component of the robot system, in particular by controlling the large number of actuators. The robot system has a measuring system configured to measure an initial value for each of the degrees of freedom. The robotic apparatus has at least one computing unit configured to carry out a method as disclosed herein in which, on the basis of an initial status given in the form of the measured initial values, items of position information of at least two discrete reference points of the first component in respect of one another are determined. Additionally, on the basis of the initial status, further items of position information of at least two discrete further reference points of the second component in respect of one another are determined. Also, dependent on the initial status, the items of position information and the further items of position information a trajectory is planned for the robot system, which transfers the robot system from the initial status into a target status of the robot system.

According to at least one embodiment of the robot system, the robot system contains a medical imaging modality having the first component and a patient couch having the second component.

According to at least one embodiment of the robot system, the first component corresponds to a C-arm for X-ray-based imaging or is rigidly attached to the C-arm.

According to at least one embodiment of the robot system, a first reference point of the at least two reference points corresponds to a center of the C-arm and a second reference point of the at least two reference points lies on an, in particular straight, line, which connects an X-ray detector of the C-arm to an X-ray collimator of the C-arm and runs through the center of the C-arm.

According to at least one embodiment of the robot system, the C-arm is mounted and/or guided in such a way that the C-arm may be orbitally rotated about a first axis of rotation and may be rotated about a second axis of rotation, which is perpendicular to the first axis of rotation, wherein the orbital rotation about the first axis of rotation and the rotation about the second axis of rotation correspond to mutually independent degrees of freedom of the large number of degrees of freedom.

Further designs of the robot system follow directly from the different embodiments of the method of trajectory planning, and vice versa. In particular, a robot system is configured to carry out a method of trajectory planning or carries out such a method.

According to a further aspect, a computer program having commands is disclosed. When the commands are executed by an apparatus for data processing, in particular an apparatus for data processing, the commands prompt the apparatus for data processing to: (1) obtain an initial status of a medical robot system, wherein a pose of a first component of the robot system may be changed independently of a pose of a second component of the robot system, in the form of measured initial values for each degree of freedom of a large number of degrees of freedom of the robot system; (2) determine items of position information of at least two discrete reference points of the first component in respect of one another on the basis of the initial status; (3) determine further items of position information of at least two discrete further reference points of the second component in respect of one another on the basis of the initial status; and (4) plan a trajectory for the robot system, which transfers the robot system from the initial status into a target status of the robot system, dependent on the initial status, the items of position information and the further items of position information.

When the commands are executed by a robotic apparatus, in particular the at least one computing unit of the robotic apparatus, the commands prompt the robotic apparatus, for example, to carry out a method of trajectory planning.

According to a further aspect, a computer-readable storage medium is disclosed, which stores a computer program.

The computer program and the computer-readable storage medium may each be comprehended as a computer program product having the commands.

A computing unit may refer to a data processing unit that contains a processing circuit. The computing unit may process data for carrying out computing operations, therefore. These possibly also include operations to carry out indicated instances of access to a data structure, for example a look-up table (LUT).

The computing unit may include one or more computer(s), one or more microcontroller(s), and/or one or more integrated circuit(s), (e.g., one or more application-specific integrated circuit(s) (ASIC), one or more field programmable gate array(s) (FPGA), and/or one or more system(s) on a chip (SoC)). The computing unit may also contain one or more processor(s), (e.g., one or more microprocessor(s), one or more central processing unit(s) (CPU), one or more graphics processing unit(s) (GPU), and/or one or more signal processor(s), such as one or more digital signal processor(s) (DSP)). The computing unit may also include a physical or a virtual group of computers or other units.

In different exemplary embodiments, the computing unit includes one or more hardware and/or software interface(s) and/or one or more memory unit(s).

A memory unit may be configured as a volatile data memory, (e.g., as a dynamic random access memory (DRAM) or static random access memory (SRAM)), or as a non-volatile data memory, (e.g., as a read-only memory (ROM), as a programmable read-only memory (PROM), as an erasable read-only memory (EPROM), as an electrically erasable read-only memory (EEPROM), as a flash memory or flash EEPROM, as a ferroelectric random access memory (FRAM), as a magneto-resistive random access memory (MRAM), or as a phase-change random access memory (PCRAM)).

Where it is mentioned that a component of the robotic apparatus, (e.g., the at least one computing unit of the robotic apparatus), is adapted, designed, configured, or the like to perform or implement a particular function, to achieve a particular effect, or to serve a particular purpose, this may be understood in such a way that the component, beyond the basic or theoretical usability or suitability of the component for this function, effect or this purpose is specifically and actually capable of performing or implementing the function, achieving the effect or serving the purpose, by way of appropriate adjustment, programming, physical embodiment, etc.

Further features of the disclosure may be found in the claims, the figures, and description of the figures. The features and feature combinations previously mentioned in the description and the features and feature combinations mentioned below in the description of the figures and/or shown in the figures may be encompassed by the disclosure not only in the respectively disclosed combination, but also in other combinations. In particular, embodiments and feature combinations, which do not have all features of an originally worded claim, may also be encompassed by the disclosure. Furthermore, embodiments and feature combinations, which go beyond the feature combinations presented in the back-references of the claims or deviate herefrom, may be encompassed by the disclosure, moreover.

The disclosure is explained in more detail below with reference to specific exemplary embodiments and associated schematic drawings. Identical or functionally identical elements may be provided with the same reference characters in the figures. The description of identical or functionally identical elements will not necessarily be repeated in respect of different figures.

DETAILED DESCRIPTION

Figure 1:
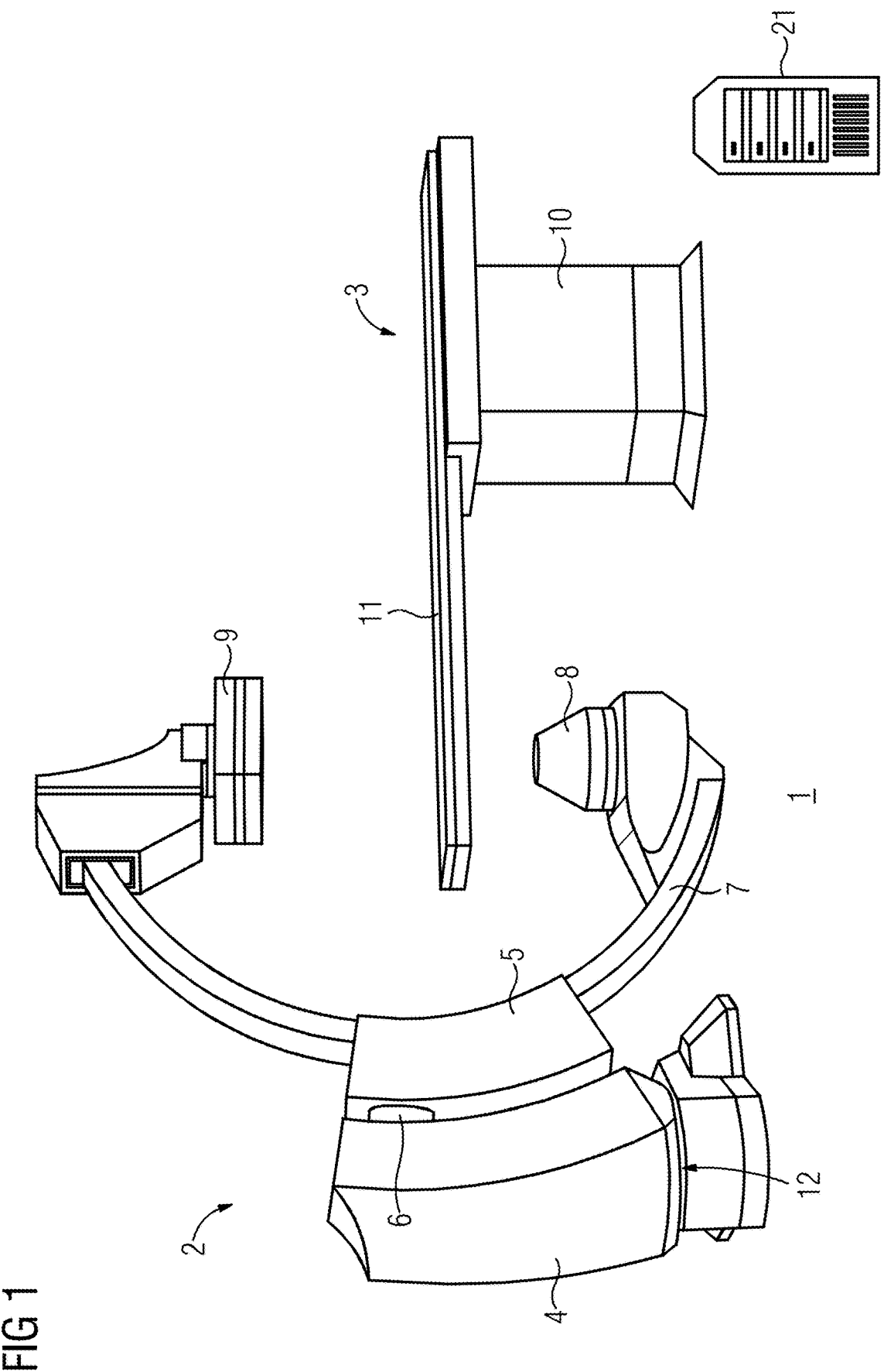
FIG. 1 depicts a schematic representation of an exemplary embodiment of a robotic apparatus.

FIG. 1 schematically shows an exemplary embodiment of a robotic apparatus having a robot system 1 and a computing unit 21.

The robot system 1 is configured as a C-arm system having a, for example mobile, robot stand 2, which contains a C-arm 7, and a patient couch 3.

The patient couch 3 has a table column 10 and a supporting plate 11 arranged on the table column 10 for a patient to lie on. The supporting plate 11 may be translationally moved in one, two, or three direction(s) and/or be rotated about one, two, or three axes of rotation in respect of the table column 10.

The robot stand 2 has a base 4, which has a swivel joint 12. A C-arm mount 5 is rotatably connected to the base 4 by a further swivel joint 6. The C-arm 7 is movably attached to the C-arm mount 5 in respect of an orbital rotation of the C-arm 7. In this example, the robot stand 2 has three rotatory degrees of freedom and may be configured to also move translationally, moreover.

Figure 2:
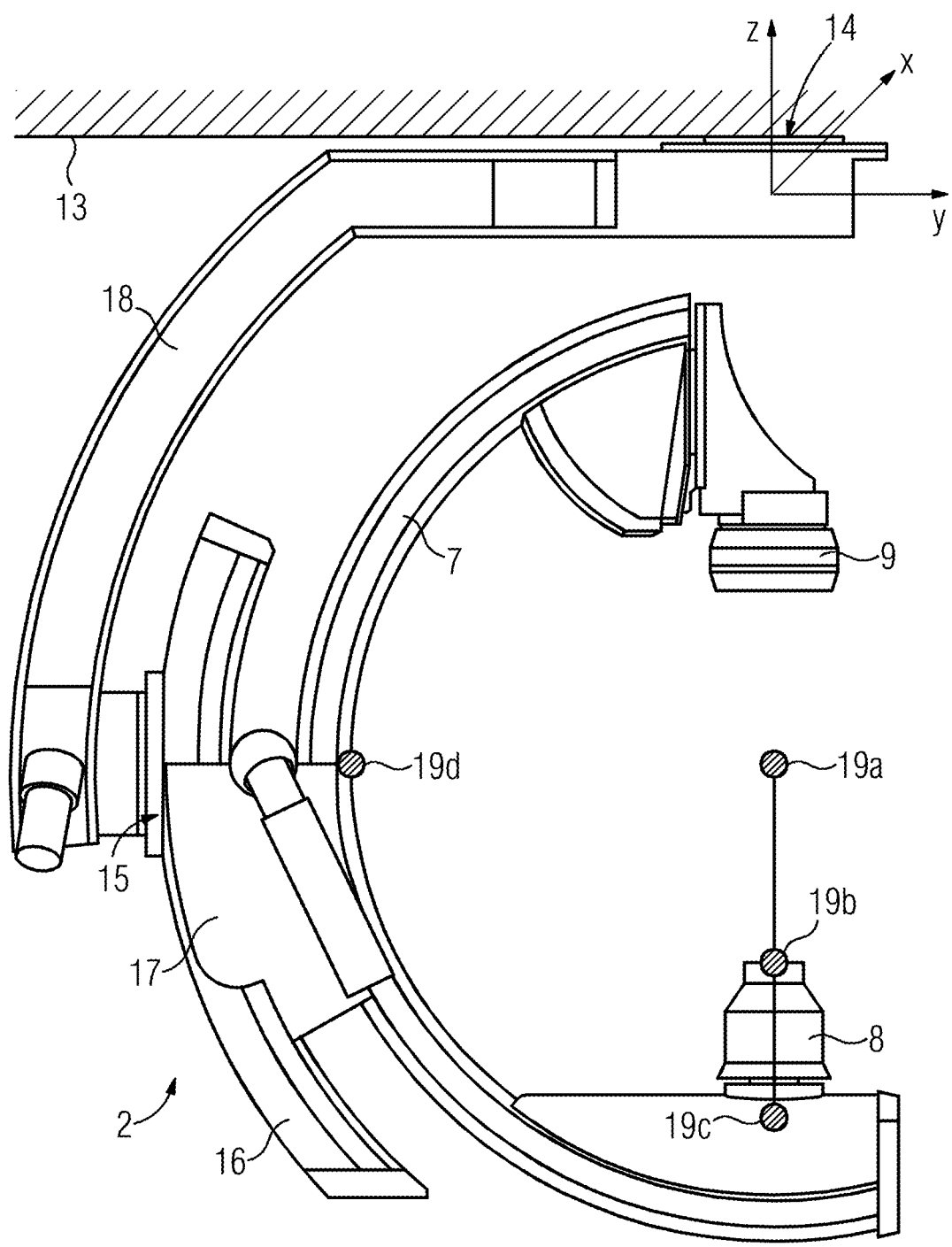
FIG. 2 depicts a schematic representation of a robot stand of a further exemplary embodiment of a robotic apparatus.

FIG. 2 schematically represents a robot stand 2 of a robot system 1 of a further exemplary embodiment of the robotic apparatus. This robot stand 2 is designed, by way of example, as a C-arm system mounted on the ceiling 13.

The robot system 1 has an actuator system (not represented), which contains a large number of actuators and a control unit for controlling the large number of actuators. The degrees of freedom of the robot stand 2 may consequently be changed independently of the degrees of freedom of the patient couch 3, or vice versa. A measuring system (not represented) of the robot system 1 may measure an initial value for each of the degrees of freedom of the entire robot system 1, for example by way of a measurement of the statuses of the large number of actuators.

On the basis of the measured initial values, which define an initial status of the robot system 1, the computing unit 21 may determine items of position information of at least two discrete reference points 19a, 19b, 19c, 19d of the robot stand 2 in respect of one another further items of position information of at least two discrete further reference points 20a, 20b, 20v, 20d, 20e, 20f (see for example FIG. 4) of the patient couch 3 in respect of one another. Dependent on the initial status, the items of position information and the further items of position information, the computing unit 21 may plan a trajectory for the robot system 1, which transfers the robot system 1 from the initial status into a target status.

According to the disclosure, a concept for carrying out collision-avoiding and safe robot movements in the three-dimensional space may be implemented. Different algorithms, which use one or more sub-robotic movement strategies, may be derived from this concept. The concept is suitable for use in medical robotics, for example, in interventional angiography. The application of the concept is not restricted to the field of medical robotics, however, but may be used in many fields of robotics to achieve high-level path planning of robots.

A robot system 1, mounted on the ceiling 13, for interventional angiography is assumed below. The same concept may also be applied to other angiography or imaging robots, however.

The robot system 1 contains a robot stand 2 and a patient couch 3. FIG. 2 shows the robot stand 2 in a side view. A C-arm 7 of the robot stand 2 has a detector 9, in particular X-ray detector, at the upper end of the C-arm 7 and a collimator 8 and/or an X-ray source at the lower end of the C-arm 7. The robot stand 2 may be positioned in many different alignments, for example, so the desired angular position of the X-ray beam from the collimator 8 to the detector 9 may be achieved. As a rule, the X-ray beam passes through the body of a patient, making a different view of the body of the patient possible in each angular position.

The robot stand 2 has, in particular, a main arm 18, which is attached to the ceiling 13 by a rotatable connector 14.

The main arm 18 and the entire robot stand 2 may move along the y-axis, which is parallel to the ceiling 13. For example, a reference point along the y-axis is selected and the movement of the robot stand 2 is measured starting from this reference point. Here and below RLMY designates the position of the robot stand 2 along the y-axis.

The main arm 18 and the entire robot stand 2 may rotate about the z-axis, which is perpendicular to the ceiling 13, in particular the rotatable connector 14. Viewed along the z-axis, the robot stand 2 may be rotated either clockwise or counterclockwise about the z-axis.

An intermediate arm 16 is attached to the main arm 18 by a rotatable connector 15. The C-arm 7 is attached to the intermediate arm 16 by a slide 17.

When the main arm 18 rotates about the z-axis, therefore, the entire robot stand 2 also rotates, in particular the C-arm 7. The angular position of the robot stand 2 about the z-axis is designated RRMZ. The position RRMZ reflects, in particular, the angular position of a motor for rotation about the z-axis, which is arranged, in particular, on the connector 14. It may be determined, for example, by an appropriate rotary encoder.

The C-arm 7 may be rotated on the connector 15, together with the intermediate arm 16, about the y-axis, with the main arm 18 remaining fixed. An appropriate motor is arranged on the connector 15, in particular. The position RRMY reflects, in particular, the angular position of this motor for rotation about the y-axis. It may be determined, for example, by an appropriate rotary encoder.

The C-arm 7 is attached to the intermediate arm 16 by the slide 17 such that it may slide, independently of the rotational movement about the y-axis, along the intermediate arm 16, so a rotation about the x-axis results, which is also referred to as an orbital rotational movement of the C-arm 7. This orbital rotational movement of the C-arm 7 may be carried out independently of a movement of the intermediate arm 16 and/or of the main arm 18. The orbital rotation may also be carried out by a motor, which is arranged at a connection of the intermediate arm 16 to the C-arm 7. The position RRMX reflects, in particular, the angle of this motor for rotation about the x-axis. It may be determined, for example, by an appropriate rotary encoder.

Figure 3:
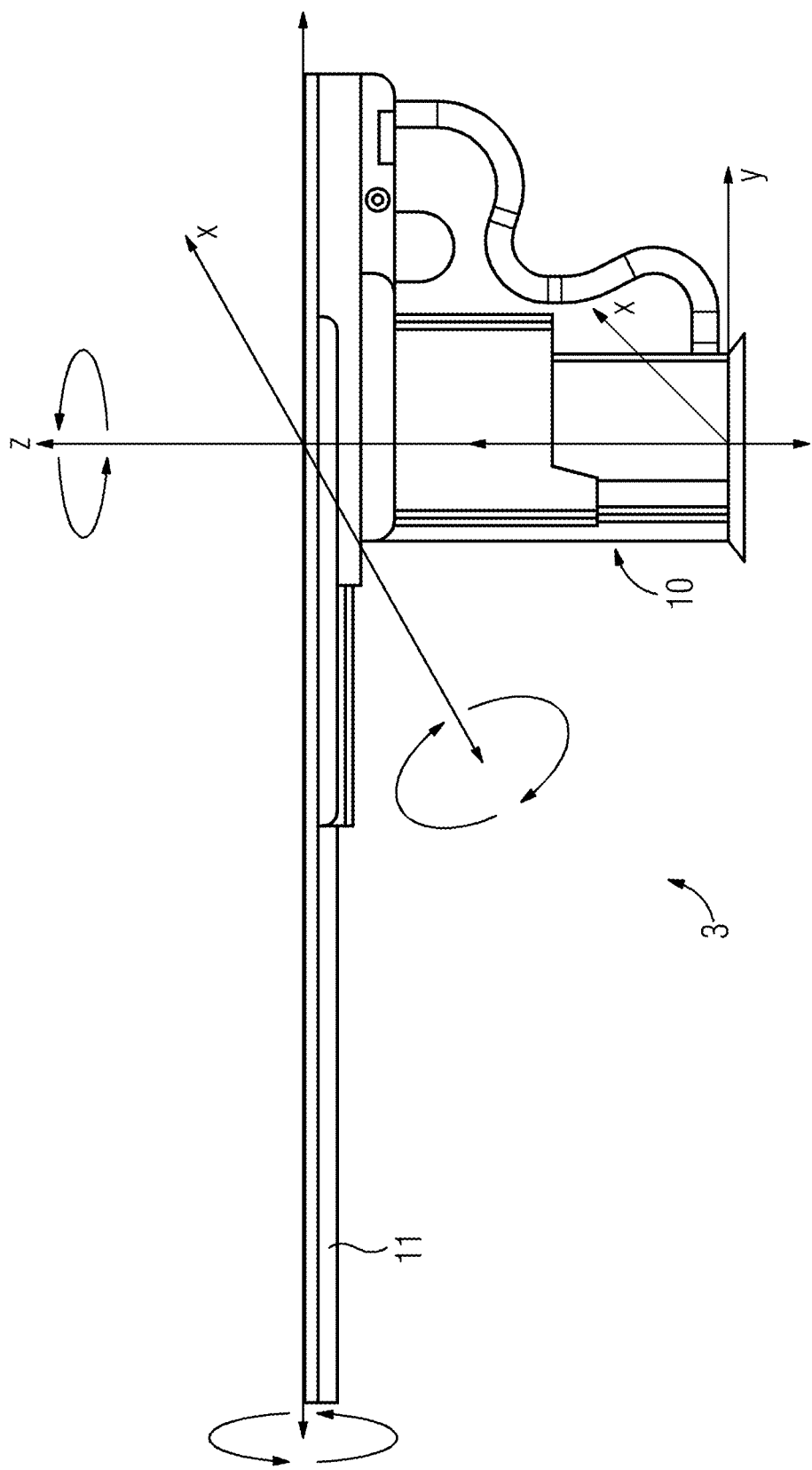
FIG. 3 depicts a schematic representation of a patient couch of a further exemplary embodiment of a robotic apparatus in a side view.

FIG. 3 represents a side view of the patient couch 3, also referred to as a patient table, having a supporting plate 11 on which a patient may be placed and which may also be referred to as a tabletop. The supporting plate 11 is supported by a table column 10.

The patient couch 3 may, analogously to RLMY, execute a longitudinal movement along the y-axis, with only the supporting plate 11 being moved, not the table column 10. TLMY designates the position of the supporting plate 11 in respect of a corresponding reference position. Furthermore, the supporting plate 11 may be moved along an x-axis and a z-axis. The corresponding positions are designated TTMX and TVMZ, respectively.

The rotation of the supporting plate 11 z-axis is given by the position TRMZ, which corresponds to the angular position of an appropriate motor and may be determined by an associated rotary encoder. This movement may also be referred to as table rotation. The rotation of the supporting plate 11 y-axis is given by the position TRMY, which corresponds to the angular position of an appropriate motor and may be determined by an associated rotary encoder. This movement may also be referred to as rocking movement. The rotation of the supporting plate 11 x-axis is given by the position TRMX, which corresponds to the angular position of an appropriate motor and may be determined by an associated rotary encoder. This movement may also be referred to as table inclination.

The instantaneous status of the robot stand 2, given by RLMY, RRMZ, RRMY, RRMX, the instantaneous status of the patient couch 3, given by TLMY, TTMX, TVMZ, TRMZ, TRMY, TRMX, and possibly dimensions of the robot stand 2 and dimensions of the patient couch 3 may be comprehended as direct input data, as data, which may be directly measured or may be determined without further data processing being necessary, therefore. Mechanical parameters of the robot system 1, boundary points of robot arms or motors may also be direct input data.

Derived input data may be data that cannot be directly measured or is not directly available and therefore a certain processing effort is required to make it available. Such data may be discrete spatial reference points, which represent the current position of the robot stand 2 and/or the patient couch 3. Such a discrete reference point may be situated at any location of the robot stand 2 or the patient couch 3 and may be derived from the instantaneous status of the robot system 1, the instantaneous status of the robot stand 2 and the instantaneous status of the patient couch 3, therefore.

FIG. 2 represents four exemplary reference points 19a, 19b, 19c, 19d of the robot stand 2. The reference point 19a is, for example, a required reference point in the center of the C-arm 7. Two further reference points 19b, 19c are arranged above or below the collimator 8. One of the two reference points 19b, 19c may likewise be required, whereas the second may be optional. A further optional reference point 19d is situated, for example, on the C-arm 7 or the slide 17.

The reference points 19a, 19b, 19c, 19d may be linked together to obtain three-dimensional vectors. These vectors help to generate a clear understanding of the position of the robot stand 2. How these vectors may be used for position control of the robot system 1 will be described further below. If required, further reference points may be added to the robot stand to create more robust position control conditions.

Figure 4:
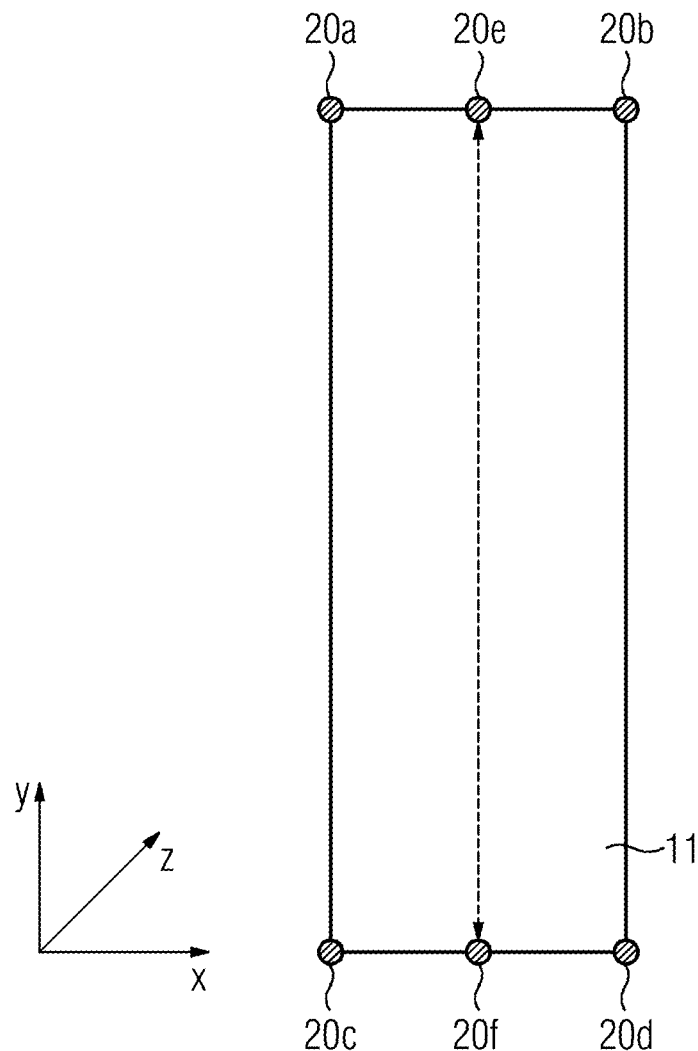
FIG. 4 depicts a schematic representation of a patient couch of a further exemplary embodiment of a robotic apparatus in a plan view.
Figure 5:
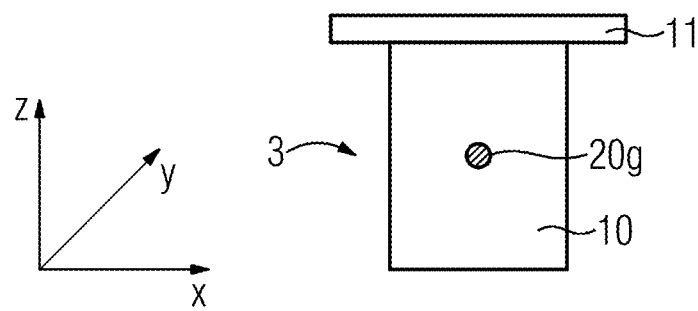
FIG. 5 depicts a schematic representation of a patient couch of a further exemplary embodiment of a robotic apparatus in a front view.

FIG. 4 and FIG. 5 represent exemplary reference points 20a, 20b, 20c, 20d, 20e, 20f, 20g of the patient couch 3. The reference points 20a, 20b, 20c, 20d are situated, for example, at the four corners of the supporting plate 11. The optional reference points 20e, 20f may be situated, for example, centrally on the short sides of the supporting plate 11. The reference point 20g is situated, for example, centrally in the table column 10.

The reference points 20a, 20b, 20c, 20d, 20e, 20f, 20g may be linked together to obtain three-dimensional vectors. These vectors help to generate a clear understanding of the position of the patient couch 3. How these vectors may be used for position control of the robot system 1 will be described further below.

Medical methods may require different setting options for the angiographic robot system 1. Put simply, the robot stand 2 and the patient couch 3 may be freely aligned to achieve the desired LAO and cranial setting. Depending on the body size of the patient, robot stand 2 and patient couch 3 may be interlocked in many different combinations. That is to say, it is difficult to resolve the position manually such that the patient is easily accessible, for example for a doctor.

Owing to the large number of degrees of freedom of the robot system 1, as described above, the number of combinations is potentially so high that, owing to the computing power required for conventional model-based automatic path planning algorithms, it may be regarded as almost infinite. The present concept enables the movement of the robot stand 2 and the patient couch 3 to be automatically brought from any initial status into a target status in which robot stand 2 and the patient couch 3 are no longer interlocked. The corresponding algorithm may be referred to as a complex position resolver.

The following aims, inter alia, may consequently be achieved:

A generic method is disclosed, which covers all clinically relevant positions and maximizes the coverage beyond the clinically relevant positions.

A movement pattern of the robot system 1, which may be regarded as safe, is achieved.

A movement pattern of the robot system 1, which actively maximizes the distance between patient and robot system 1, is achieved.

A movement pattern, which is consistent throughout the entire life of the robot system 1, is achieved. This means that the robot system 1 for given initial status and target status the same trajectory results.

A deterministic robot movement is achieved. This means that, using the current position, a person may predict how the robot system 1 will move.

A shorter reaction time is achieved, if it is possible on the basis of the hardware and/or system specifications.

Faster movement planning is achieved, if it is possible on the basis of the hardware and/or system specifications.

The planning time is independent of the initial status of the robot system 1.

The complex position resolver may be comprehended as a robotic movement strategy, which is composed of robotic sub-movement strategies.

In the medical context, the sub-movement strategies make control of the following movements possible, for example: cranial/caudal movement; LAO/RAO movement; cranial/caudal movement with minimal or no change in the LAO/RAO position; and/or shifting of the patient couch 3 into a safe status, at which the risk of a collision of the patient and/or the patient couch 3 with the robot stand is minimized.

In addition, values for LAO/RAO may be ascertained, which minimize the risk of collisions with the patient or bruising of the patient.

A specific application for the complex position resolver will be described below.

An emergency situation may occur during interventional angiography or another procedure. In extreme cases, a doctor may have to carry out cardiopulmonary resuscitation (CPR) on the patient. Such emergencies are highly time-critical, and the doctor requires access to the patient as quickly as possible to be able to carry out CPR. In some cases, the situation may occur where the robot system 1 is interlocked in such a complex way that the patient may no longer be reached. In addition, the status of the robot system 1 may be so complex that manual repositioning of the robot system 1, to obtain access to the patient, requires a lot of time. In such cases, faster automatic repositioning of the robot system 1 into a status in which access to the patient is possible, may save a lot of time. If such an automatic movement may be carried out reliably and quickly, the doctor has to give the robot system 1 just one corresponding command. If the automatic movements are deterministic, moreover, an experienced doctor may even begin preparing for CPR while the robot system 1 is being repositioned.

In such cases, for example, the following sequence of partial strategies for faster repositioning of a robot system 1 may be used to obtain access to the patient: (1) Longitudinal movement of the patient couch 3 along the y-axis; (2) Cranial movement with minimal or no change in the LAO; (3) Bringing the patient couch 3 into a safe status in which the risk of a collision is minimized; (4) LAO movement for minimal risk of bruising/collision to the patient; (5) Vertical movement of the patient couch 3 along the z-axis; (6) Transversal movement of the patient couch 3 along the x-axis; (7) LAO movement; (8) Vertical movement of the patient couch 3 along the z-axis; (9) Rotational movement of the patient couch 3 about the x-axis; (10) Rotational movement of the patient couch 3 about the y-axis; (11) Longitudinal movement of the robot stand 2 along the y-axis.

This course of movement may be executed as required or depending on desired quality and safety goals, either simultaneously, partially simultaneously, or successively, in particular in the order. With this course of movement, the robot system 1 may be brought quickly from any complex status into a status in which access to the patient is possible.

Further technical details of the complex position resolver will be explained below.

As mentioned above, correct functioning of the complex position resolver may require geometric input data, in particular direct and derived input data. The complex position resolver may use derived input data to generate additional input data, as will be explained below.

FIG. 2 shows a vector, which points from the reference point 19a to the reference point 19b or to the reference point 19c. This vector will be referred to below as the C-arm vector-of-interest, CVOI for short.

The complex position resolver may have, for example, the following sections: (1) Dual plane vector controller; (2) Mono plane controller; (3) Patient couch relocalizer; (4) Robot stand forward kinematics; (5) Robot stand optimum solution identifier; and/or (6) Patient couch point-of-interest calculator.

The dual plane vector controller controls the alignment of the CVOI. This is controlled by two different strategies: mono-rotation control and dual-rotation control.

Figure 6:
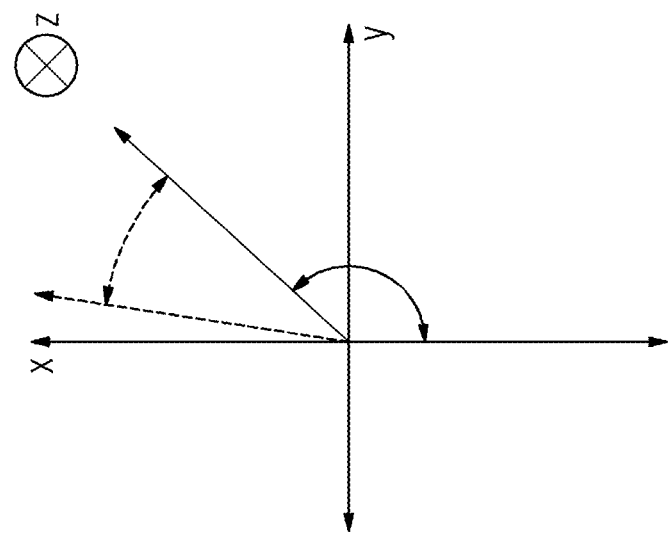
FIG. 6 depicts a schematic representation of a patient couch of a further exemplary embodiment of a robotic apparatus in a plan view.
Figure 6:
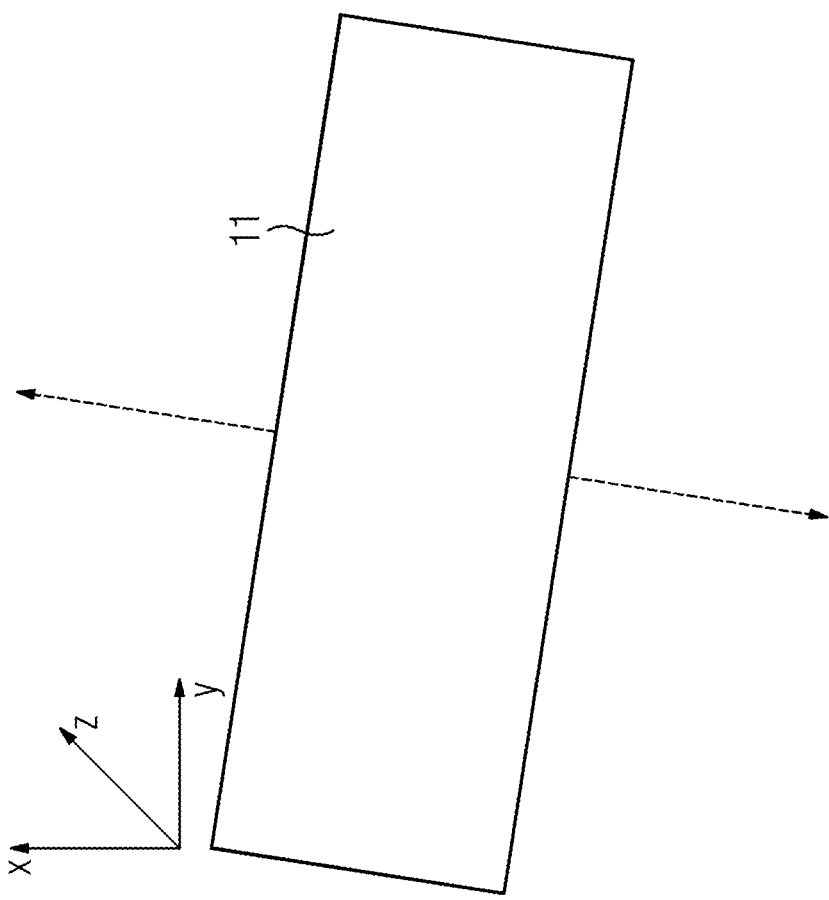

Mono-rotation control controls the alignment of the CVOI in the x-y-plane. Changes, which are caused in other planes due to the alignment control in the x-y-plane, are not taken into account in this case. This control of the angle of the CVOI is visualized in FIG. 6. The plan view of the patient couch 3 or the supporting plate 11 may be seen on the left. A vector (arrow with dotted line in FIG. 6) is calculated, which is perpendicular to the patient couch 3. The direction of this vector is determined on the basis of the alignment of the collimator 8 in the x-y-plane in relation to the supporting plate 11. On the right, FIG. 6 shows the plan view of the reference coordinate system of the robot stand 2. The vector perpendicular to the patient couch 3 is transformed from the reference coordinate system of the patient couch 3 into reference coordinate system of the robot stand 2. The angle between the CVOI (arrow with solid line, on the right in FIG. 6) and the vector perpendicular to the patient couch 3 is controlled. The aim is to keep this angle as close as possible to 0.

In other words, the angle of the CVOI in the x-y-plane is to be ascertained by way of this section and the CVOI set perpendicular to the patient couch 3. This section is only activated, in particular, if particular specified safety criteria are met, as will be explained below.

Figure 7:
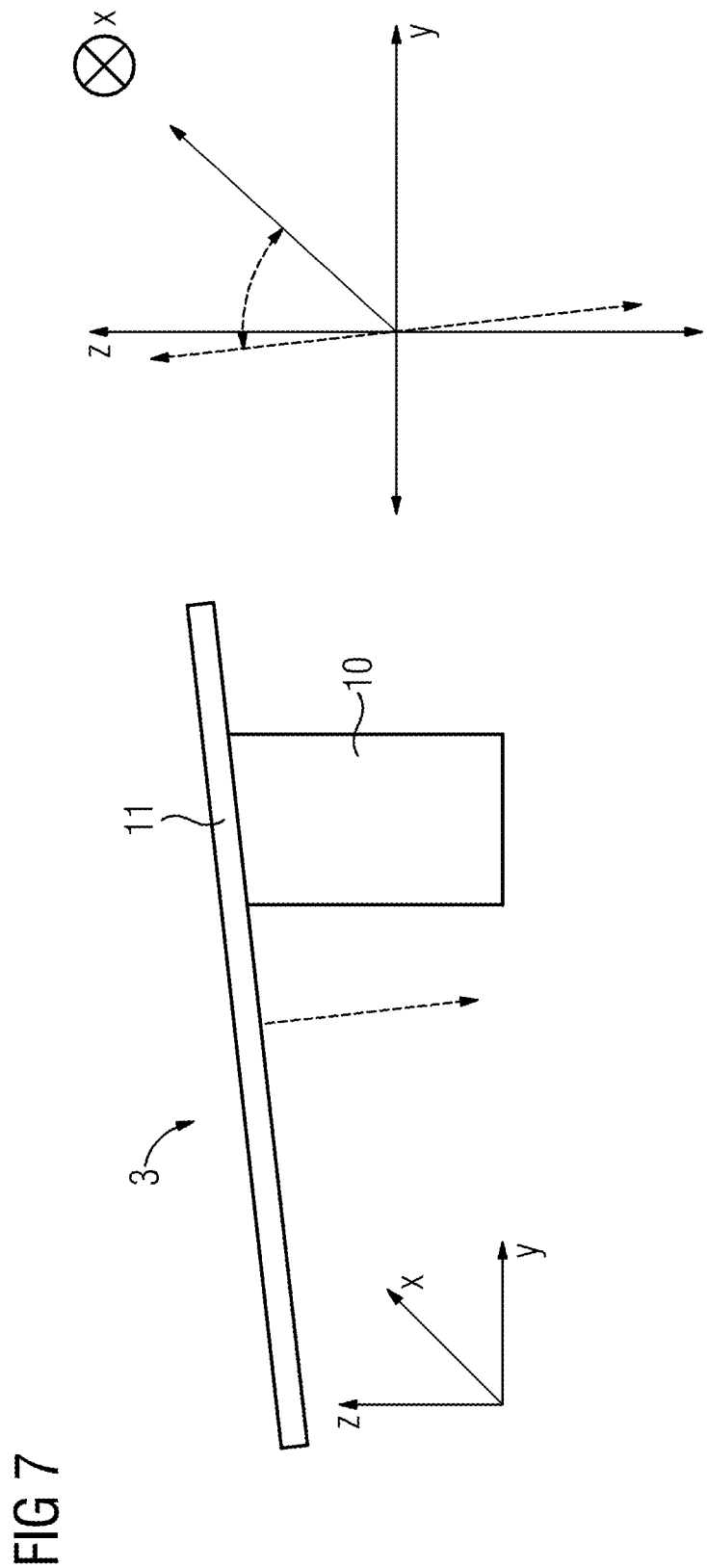
FIG. 7 depicts a schematic representation of a patient couch of a further exemplary embodiment of a robotic apparatus in a side view.

The section "dual rotation control of the algorithm" controls the alignment of the CVOI in the y-z-plane and may correct or take into account possible changes, which are caused in the x-z-plane by the alignment control in the y-z-plane. FIG. 7 schematically represents the angular control. On the left, FIG. 7 shows the inclined supporting plate 11, TRMX therefore. The vector perpendicular to the supporting plate 11 (arrow with dotted line in FIG. 7) is generated and its effective impact in the 3-dimensional space is calculated. On the basis of the instantaneous alignment of CVOI (arrow with solid line, on the right in FIG. 7), the corresponding effective impact is applied to CVOI, the remaining difference between the vector perpendicular to the supporting plate 11 and the CVOI is controlled.

In other words, the angle of the CVOI in the y-z-plane is to be ascertained by way of this section and the CVOI aligned perpendicular to the supporting plate 11, while the impacts in the x-z-plane are minimized. In other words, the angle of the CVOI in the x-z-plane may remain the same or change only minimally. This section is, in particular, always active.

The section "mono plane controller of the algorithm" controls the alignment of the CVOI in the x-z-plane. This alignment of the CVOI is controlled, for example, by two different strategies: patient couch-dependent control and patient couch-independent control.

Figure 8:
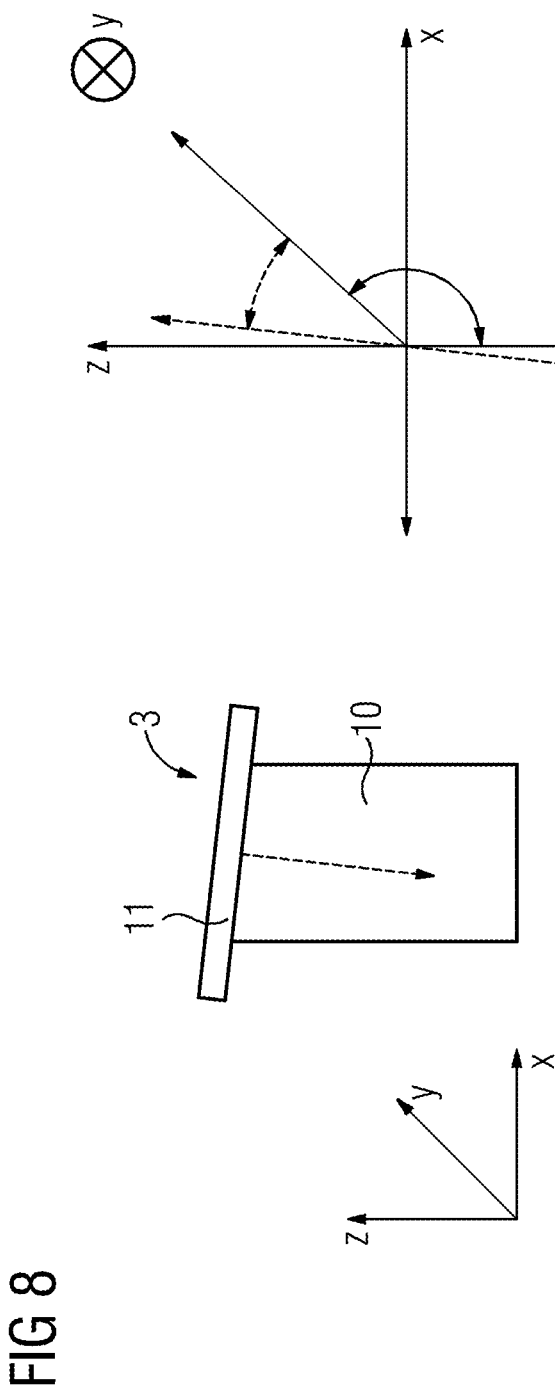
FIG. 8 depicts a schematic representation of a patient couch of a further exemplary embodiment of a robotic apparatus in a front view.

With patient couch-dependent control, the alignment of the CVOI in the x-z-plane is controlled dependent on the current position of the patient couch 3. This section uses the point-of-interest information of the patient couch 3 to derive the required alignment of the CVOI in the x-z-plane. In addition, all changes are taken into account, which result either in the y-z-plane or in the x-y-plane due to the alignment control in the x-z-plane. FIG. 8 schematically represents the control of the angle. On the left, FIG. 8 shows the front view of the patient couch 3, with it being possible to see TRMY. The vector perpendicular to the supporting plate 11 (arrow with dotted line in FIG. 8) is generated and its effective impact in the 3-dimensional space is calculated. On the basis of the instantaneous alignment of the CVOI (arrow with solid line, on the right in FIG. 8), the corresponding effective impact is applied to the CVOI, the remaining difference between the vector perpendicular to the supporting plate 11 and the CVOI is controlled.

In other words, the angle of the CVOI in the x-z-plane is ascertained and the CVOI in the x-z-plane is aligned with this angle by way of this section, while the alignment of the CVOI in the y-z- and x-y-planes is kept at the desired value. This section is, for example, always active.

With patient couch-independent control, the alignment of the CVOI in the x-z-plane is controlled independently of the current position of the patient couch 3. In this section, the angle of the CVOI in the x-z-plane is ascertained, which minimizes the risk of bruising and/or collision for the patient and enlarges the scope for movement of the patient couch 3. In other words, the angle of the CVOI in the x-z-plane is ascertained and the CVOI aligned with this angle in the x-z-plane by way of this section, while the alignment of the CVOI in the y-z- and x-z-planes is kept at the desired value. This section is, for example, always active.

The section "patient couch relocalizer" controls TTMX and TVMZ of the patient couch 3. It uses the point-of-interest information of the patient couch 3 and the information relating to CVOI to ascertain the required displacement of the patient couch 3 in the TTMX and TVMZ directions. In other words, the patient couch 3 is displaced such that the point-of-interest moves as far as possible in the direction of the origin of the CVOI, in particular of the reference point 19a therefore, with the instantaneous position of the robot stand 2 being taken into account. This section is only activated, for example, if particular criteria are met, as explained below.

The section "patient couch point-of-interest calculator" uses the available information about CVOI to calculate the above-mentioned point on the patient couch 3, which is referred to as the point-of-interest of the patient couch 3. The point-of-interest may be regarded as additional information, which is generated on the basis of the derived data and the instantaneous position of the robot stand 2. Other sections of the complex position resolver may use the point-of-interest to bring the patient couch 3 into a position, which is safer and provides a lower risk of collision, and/or to ascertain the desired angle of alignment of the CVOI in the x-z-plane.

The section "robot stand forward kinematics" supplies the items of position information of the robot stand 2. For given values of RRMZ, RRMY, and RRMX, this section finds the corresponding values for CVOI, which represent the given values for RRMY, RRMZ, and RRMX or for the given values of RRMZ and RRMX, and the angles of CVOI in the x-z-plane and in the y-z-plane.

The section "robot stand optimum solution identifier" calculates the optimum RRMY, and RRMX values of the robot stand 2 for given RRMZ and CVOI. In addition, this section supplies information about the integrity of the optimum values for RRMY and RRMX. For example, the specified RRMY and RRMX values may be limited owing to mechanical restrictions, so the CVOI may not be achieved. In such cases, this section returns the best possible RRMY and RRMX values, which are closest to the given CVOI with given RRMZ. This part of the algorithm may be freely adjusted, as required, to find an optimum solution. The implementation of this section for CPR concentrates on the provision of a solution, which is close to the current RRMX and RRMY values of the robot stand 2 and indicates a reduced or minimized risk of collision.

The implementation of different sections of the complex position resolver will be described in more detail below.

The section "robot stand optimum solution identifier" supplies the positions RRMY, RRMX, which represent a given CVOI with a given RRMZ. It covers information about how CVOI and RRMZ are used to determine RRMY, RRMX, which represent the given CVOI.

The CVOI provided to this section as an input is influenced by the RRMZ rotation of the robot stand 2. To eliminate the influence of RRMZ on CVOI, CVOI may be rotated about the z-axis in that the value exactly opposite the RRMZ position is specified. The vector-of-interest aligned with the z-direction results from this and is referred to as VOIzA.

In some situations, for example, if the length of the projection of VOIzA in the x-z-plane is shorter than a specified limit value, it may be safer and more reliable to return the current RRMY value of the robot stand to prevent RRMY movement of the robot stand 2. The decision about how the algorithm may react in this case may be made as necessary.

To ascertain the reliability of the projection of VOIzA the following sequence, for example, may be used. The coordinates of VOIzA are referred to as VOIzAx, VOIzAy, and VOIzAz. Firstly, the three-dimensional length of VOIzA, $$L3D = \sqrt{VOIzAx^2 + VOIzAy^2 + VOIzAz^2},$$

and the length of the projection of the VOIzA in the x-z-plane, $$L2D = \sqrt{VOIzAx^2 + VOIzAz^2},$$

are calculated and the minimum length of the projection of VOIzA in the x-z-plane, $$LL = L3D * \cos(\emptyset),$$

is determined, with $\emptyset$ being the angle, which is used for selection of the minimum length. The value of $\emptyset$ may be selected as necessary on the basis of the possibilities of the system, for example 89°.

For example, it may be assumed that if L2D is shorter than or equal to LL, RRMY cannot be reliably calculated. Otherwise, RRMY may be ascertained, for example by the following method. The angle $\theta xz$ of VOIzA in the x-z-plane is calculated:

$$Fxz = \frac{VOIzAx}{L2D},$$

$$\theta xz = \cos^{-1}(|Fxz|).$$

RRMY is measured starting from a fixed reference, $\theta xz$ is used, and the absolute angle of VOIzA in the x-z-plane is measured.

The measured absolute angle is the value of RRMY. RRMY is a rotational movement, however, that is to say, the value of RRMY may be obtained in the system by a rotation clockwise and a rotation counterclockwise. This means that there are two solutions for RRMY. If one solution is $\pm\theta$, the other is $\pm\theta \pm 360$.

On the basis of the requirements of the application, restrictions may be applied to select the most suitable solution. For example, the aim is to reach the target quicker and with minimal movement of the robot stand 2. For this purpose, a condition may be added, which measures the required movement of the robot stand 2 from the instantaneous RRMY value to each available solution of RRMY. The solution, which comes closest to the instantaneous RRMY, is selected as the optimum RRMY solution.

As soon as the RRMY solution has been obtained, RRMX may be obtained by the following method, for example. VOIzA is aligned in respect of the z-axis, but not necessarily in respect of the x-axis. Because the obtained value of RRMY represents the angle of VOIzA in the x-z-plane, VOIzA is rotated about the y-axis by the value RRMY to align VOIzA with the x-axis, too. The resulting vector, which is aligned in relation to the z-axis and the x-axis, is referred to as VOIzxA. This also has three coordinates VOIzxAx, VOIzxAy, and VOIzxAz. The length of the projection of VOIzxA in the y-z-plane is:

$$L2D = VOIzxAy^2 + VOIzxAz^2.$$

The angle $\theta yz$ of VOIzxA in the y-z-plane is determined:

$$Fyz = \frac{VOIzxAy}{L2D},$$

$$\theta yz = \cos^{-1}(|Fyz|).$$

RRMX is measured starting from a fixed reference, $\theta yz$ is used, and the absolute angle of VOIzxA in the y-z-plane is measured.

Analogously to RRMY there are two solutions for RRMX. Here too, for example, RRMX may therefore be determined such that it comes closest to the current RRMX position of the robot stand 2. The obtained solution may be regarded as the optimum RRMX solution.

For identification, additional restrictions are applied to the extent that the solutions for RRMY and RRMX correspond to mechanical and/or dynamic limits of the robot stand 2. Dynamic limits are, for example, limits, which may be imposed on the robot stand 2 to minimize the risk of bruising and/or collisions. These restrictions are dependent on the mechanics of a specific robot system 1.

These will be derived below, by way of example for a system mounted on the ceiling. The mechanical position limits of the robot stand 2 RRMY, RRMX may be ascertained from the direct input data. The maximum and minimum mechanical position limits for RRMY are MLYMax and MLYMin, respectively. The maximum and minimum mechanical position limitations for RRMX are MLXMax and MLXMin, respectively. By way of example, the following mechanical limits will be assumed for a system mounted on the ceiling: MLYMax=180°, MLYMin=−150°, MLXMax=100°, MLXMin=−100°.

The C-arm 7 of a system mounted on the ceiling may be positioned around the patient couch 3 in many ways. Some positions are so complex that when a movement of the robot stand 2 within the entire range of the mechanical limits is permitted, the risk of collisions or bruising may exist. For such positions, soft limitations may be applied in addition to the mechanical limitations. If the robot stand 2 is situated on the left or right side patient couch 3, the RRMY movement may be restricted by soft limitations, which depend on the mechanical construction of the system mounted on the ceiling. Similarly, the RRMX movement may be restricted by a soft limitation if the robot stand 2 is situated on the patient couch 3. With a system mounted on the ceiling, the motors and arms, which control RRMY and RRMX, may also be moved with RRMZ. In other words, the soft limitation that may apply to RRMY and RRMX depends on the RRMZ position of the robot stand. This may be used to derive the dynamic limits of the system.

Maximum and minimum limit values may be defined for RRMY, RRMX, which are independent of the position of the robot stand 2. These limit values are relative and are measured from the start or end of the quadrant in which the robot stand 2 is currently situated. The maximum and minimum robot-independent limits of RRMY are ILYMax or ILYMin respectively, for example ILYMax=60°, ILYMin=−60°. The maximum and minimum robot-independent limits of RRMX are ILXMax and ILXMin respectively, for example ILXMax=90°, ILXMin=−90°.

The dynamic limits of the robot stand 2 RRMY, RRMX may thus be ascertained as follows, for example. The impact factor for RRMY is Frrmy=cos(Ø) and the impact factor for RRMX is Frrmy=sin(Ø), where Ø is the current RRMZ value of the robot stand 2. The maximum and minimum dynamic limits of RRMY are DLYMax and DLYMin respectively, where:

$$\Delta max=(MLYMax-ILYMax)*Frrmy,$$

$$DLYMax=ILYMax+|\Delta max|,$$

$$\Delta min=(MLYMin-ILYMin)*Frrmy,$$

$$DLYMax=ILYMin+|\Delta min|.$$

The maximum and minimum dynamic limits of RRMX are DLXMax and DLXMin respectively, where:

$$\Delta max=(MLXMax-ILXMax)*Frrmx,$$

$$DLXMax=ILXMax+|\Delta max|,$$

$$MLXMax=-MLXMin,$$

$$ILXMax=-ILXMin,$$

$$DLXMin=-DLXmax.$$

Limit value checks and changes/saturations of RRMY and RRMX may be performed on the basis of these mechanical and dynamic limit values. If, for example, RRMY solution>DLYMax, then the RRMY solution may be limited to the corresponding quadrant, so the RRMY solution does not depart from the range of the soft limitation. If, for example, RRMY solution<DLYMin, then the RRMY solution may be limited to the corresponding quadrant, so the RRMY solution does not depart from the range of the soft limitation. If, for example, RRMY solution>MLYMax, then the RRMY solution may be limited to MLYMax. If, for example, RRMY solution<MLYMin, then the RRMY solution may be limited to MLYMin.

These conditions may be expanded to restrict the solution depending on the specified application. The same concept of the limit values and the calculation of reliable values may also be applied.

The section "patient couch point-of-interest calculator" supplies a spatial point on the patient couch 3 as a function of the instantaneous position of the robot stand 2. This spatial point, which may be referred to as a point-of-interest of the patient couch 3, permanently connects the table to the robot stand 2 in the 3-dimensional space.

The point-of-interest may be calculated as follows. On the basis of derived and direct input data, the reference points 20*a*, 20*b*, 20*c*, 20*d*, 20*e*, and/or 20*f* of the patient couch 3 may be used to derive a general straight line equation in the x-y-plane, which runs through the center of the patient couch 3 along the y-axis, as may be seen by the dotted line between the reference points 20*e* and 20*f* in FIG. 4, x=m*y+c, where m is the gradient, c the offset, x a value of TTMX and y any value of TLMY. The CVOIy value is used in this straight line equation, so the x-coordinate TPOIx of the point-of-interest TPOI is obtained. A further general straight line equation in the z-Y-plane is established by the reference points 20*a*, 20*b*, 20*c*, 20*d*, 20*e*, and/or 20*f*, which runs through the center of the patient couch 3 along the y-axis, although now in the z-y-plane, x=m*y+c, where m is the gradient, c the offset, x a value of TVMZ, and y any value of TVMY. The CVOIy value is used in this straight line equation, so the z-coordinate TPOIz of TPOI is obtained. To obtain the y-coordinate TPOIy of TPOI, TPOIy=CVOIy may be used. The coordinates of CVOI and the reference points 20*a*, 20*b*, 20*c*, 20*d*, 20*e*, and/or 20*f* are to be used for calculation in the same coordinate system, corresponding coordinate transformations are carried out, therefore.

The section "patient couch relocalizer" uses the TPOI to move the patient couch 3 as a function of the position of the robot stand 2 to a safe location. It is calculated by how much TPOI TTMX and TVMZ directions it is possible to move, in order to prevent a collision with the robot stand 2. The final TTMX and TVMZ position of the patient couch 3 may be calculated as follows. The TPOI is displaced as close as possible to the point of origin of the CVOI, reference point 19*a* therefore, which may also be represented as OCVOI=(OCVOIx, OCVOIy, OCVOIz). The required total displacement in the TTMX direction is:

$$\Delta tx=TPOIx-OCVOIx,$$

Required total displacement thein TVMZ direction is:

$$\Delta tz=TPOIz-OCVOIz.$$

The total displacement is limited by the current position of the robot stand 2. The permissible relocalization may be ascertained as follows. The safe displacement factor in the TTMX direction is given by:

$$SDFx=\sin^2(Ø),$$

and the safe displacement factor in the TVMZ direction is given by:

$$SDFz=\cos^2(Ø)$$

where Ø is the angle of projection of CVOI in the x-z-plane and where CVOI represents the current position of the robot stand.

The permitted displacement in TTMX is:

$$\Delta ax = \Delta tx * SDFx$$

The permitted displacement in TTMZ is:

$$\Delta az = \Delta tz * SDFz$$

The final position of the patient couch 3 in order to displace the TPOI as close as possible to OCVOI is as follows: position of the patient couch 3 TTMX=current position of the patient couch 3 TTMX+Δax, position of the patient couch 3 TVMZ=current position of the patient table TVMZ+Δaz.

The section "mono rotation control" orients CVOI in the x-y-plane such that, viewed from the z-axis, it is perpendicular to the supporting plate 11. It calculates the position RRMZ in order to achieve this alignment of the CVOI. This section is selectively activated, for example, when particular criteria are met. These criteria may be determined as follows.

With the aid of the x- and y-coordinates of the reference points 20a, 20c at the left-hand edge of the supporting plate 11, see FIG. 4, the general equation of the line running through these reference points 20a, 20c for the x-y-plane may be ascertained and described as follows: x=m*y+c, where m corresponds to the gradient, c the offset, x a value of TTMX and y any value of TLMY. With the CVOIy coordinate value of CVOI, the TTMX value may be obtained therefrom. This TTMX value is referred to as range end one (REO): REO=m*CVOIy+c.

Similarly, by using the reference points 20b, 20d at the right-hand edge of the supporting plate 11 and a further straight line equation, a further value of TTMX with given CVOIy is ascertained. This value of TTMX is referred to as range end two (RET). REO and RET are two limitations for TTMX with given CVOIy.

If the CVOIx coordinate value is within REO and RET, the section "mono rotation control" is, for example, not activated. Otherwise, the following method is carried out for calculation of the RRMZ position.

The following may be derived on the basis of derived and direct input data:

By the reference points 20a, 20b, 20c, 20d, 20e and/or 20f a general straight line equation in the x-y-plane is derived, which runs along the y-axis through the center of the supporting plate, as shown by the dotted line between the reference points 20e and 20f in FIG. 4, x=m*y+c. Furthermore, a straight line equation for a straight line of origin perpendicular thereto is derived: xp=mp*yp. From this equation for the perpendicular straight line of origin, a line LP is derived, which runs in the same direction as CVOI in the x-y-plane. CVOI is displaced in the same origin, so CVOI and LP go through the same origin and in general run along any directions. A triangle is formed if the open end points of CVOI and LP are joined. In order to form a triangle, the open ends of CVOI and LP are joined therefore by a line LC. Because the coordinates of the CVOI end point and of the LP end point are already known, the length of the LC may be ascertained. The angle α between CVOI and LP is calculated with the aid of the following formula:

$$\alpha = \cos^{-1}\left(\frac{Lcvoi^2 + L1p^2 - L1c^2}{2 * Lcvoi * L1p}\right).$$

By α, the alignment of LP and the alignment of CVOI in the x-y-plane a suitable reference point for changing α is ascertained and the direction of rotation determined to align the vector CVOI with LP. After selection of the direction of rotation and the change in a, a may possibly be restricted further according to specified criteria.

The RRMZ value is ascertained by the following operation: RRMZ position of the robot stand for orienting CVOI=current RRMZ position of the robot stand ±α.

Additional safety conditions may also be added to restrict the final RRMZ value. Thus, for example dependent on the mechanical construction of the robot stand 2, particular positions may be limited by applying dynamic and mechanical limit values to reduce risks of collision.

As explained above the section "dual rotation control" controls the alignment of CVOI in the y-z-plane and attempts to retain the existing alignment of the CVOI in x-z-plane.

The following data for the current position of the robot stand 2 may be ascertained by the forward kinematics of the robot stand 2:

CVOI angle in the y-z-plane: α.
CVOI angle in the x-z-plane: γ.
CVOI, which represent given RRMY, RRMZ and RRMX values: CVOI.
CVOI, which represent given RRMZ and RRMX values, aligned with the y-axis: VOIyA.

This section may be used to displace CVOI such that the desired angle is produced in the y-z-plane, while the existing angle in the x-z-plane is retained. This may be achieved as follows. The desired angle of the CVOI in the y-z-plane is θd. The actual angle of the CVOI in the y-z-plane dependent on the position of the patient couch 3 TRMX, TRMZ is β. The required rotation of the CVOI about the x-axis is Δx=θd−β, where $$\beta = \alpha - (Ftrmx * TRMX) + (Ftrmz * TRMZ).$$

In this case, TRMX is the actual value of the inclination about the x-axis, TRMZ the actual value of the rotation about the z-axis, and:

$$Ftrmx = \cos(\gamma),$$

$$Ftrmz = \sin(\gamma).$$

When Δx is calculated, the following operations may be carried out an VOIyA to align it as desired. VOIyA is rotated about the x-axis by Δx and about the y-axis by γ. The resulting vector is aligned in the y-z-plane as desired, with the existing alignment in the x-z-plane being retained.

The resulting vector and the current position of RRMZ, RRMY and RRMX are input into the section "robot stand optimum solution identifier." This returns the position of RRMY and RRMX, which represents the position of the robot stand 2 in order to achieve the desired VOIyA alignment. The situation may occur where the values of RRMY and RRMX are saturated up to the maximum achievable solution in the case of mechanical or dynamic limit values.

The patient couch-dependent control of the section "mono plane controller" aligns CVOI in the x-z-plane by the instantaneous position of the patient couch 3. In addition, the positions RRMX and RRMY are output, which represent the aligned CVOI. The following data for the current position of the robot stand 2 is ascertained by the forward kinematics of the robot stand 2:

CVOI angle in the y-z-plane: α.
CVOI angle in the x-z-plane: γ.
CVOI, which represent given RRMY, RRMZ and RRMX values: CVOI.

CVOI, which represent given RRMZ and RRMX values, aligned with the y-axis: VOIyA.

The values of Δax and Δaz may be determined as explained above. On the basis of this, the desired angle of alignment θd of CVOI in the x-z-plane are determined, for example, as follows:

When |Δaz|<|Δax|:
When |γ|<90°:

$$\theta d = 0.01°.$$

When |γ|<180°:

$$\theta d = \begin{cases} MLYMin, \gamma \leq 0 \\ MLYMax, \gamma > 0 \end{cases}$$

Otherwise:

$$\theta d = \begin{cases} -89.99, \gamma \leq 0 \\ 89.99, \gamma > 0 \end{cases}$$

Because the desired angle of alignment is now known, the following method may be carried out to derive the RRMX and RRMY positions. The actual CVOI angle in the x-z-plane dependent on the TRMY position of the patient table is β. The required rotation of CVOI about the y-axis is Δy=θd−β, where β=γ+current TRMY of the patient couch 3. CVOI is rotated about the y-axis by Δy. The desired angle of alignment in CVOI is obtained as a result.

This resulting vector and the current position of the robot stand 2 RRMZ, RRMY and RRMX are fed to the section "robot stand optimum solution identifier". This supplies the RRMY and RRMX positions, which represent the position of the robot stand 2 in order to achieve the desired CVOI alignment.

The change in the x-z-alignment may result in a change in the alignment of the CVOI in the y-z-plane, however. Accordingly, CVOI may be re-aligned in the y-z-plane, with the alignment in the x-z-plane remaining the same. The re-calculated RRMY and RRMX positions and the current RRMZ position at the section "dual rotation control" are given for this. This brings about the alignment in the y-z-plane and supplies the RRMX and RRMY positions.

These final values of RRMX and RRMY are the desired values in order to position the robot stand 2 at the location at which CVOI is aligned in the system as desired. The situation may occur where the values of RRMY and RRMX are saturated up to the maximum achievable solution in the case of mechanical or dynamic limit values.

The patient couch-independent control of the section "mono plane controller" is similar to the section patient table-dependent control. In particular, the sole difference is that the point-of-interest is not used for determining the angle θd. Instead, an approach as follows, for example, is used:

$$\theta d = \begin{cases} -89.99, \gamma \leq 0 \\ 89.99, \gamma > 0 \end{cases},$$

where β=γ.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method of trajectory planning for a medical robot system, wherein a pose of a first component of the medical robot system is configured to be changed independently of a pose of a second component of the medical robot system, the method comprising:
   determining, by at least one processor of a robotic apparatus having the medical robot system, an initial status of the medical robot system for each degree of freedom of a plurality of degrees of freedom of the medical robot system, wherein an initial value is measured;
   determining, by the at least one processor and based on the initial status, items of position information of at least two discrete reference points of the first component in respect of one another;
   determining, by the at least one processor and based on the initial status, further items of position information of at least two discrete further reference points of the second component in respect of one another;
   planning, by the at least one processor, a trajectory for the medical robot system dependent on the initial status, the items of position information, and the further items of position information; and
   transferring, by the robotic apparatus, the medical robot system from the initial status into a target status of the medical robot system along the trajectory,
   wherein the medical robot system comprises a medical imaging modality that has the first component,
   wherein the medical robot system comprises a patient couch that has the second component,
   wherein the first component corresponds to a C-arm for X-ray-based imaging or is rigidly attached to the C-arm,
   wherein a first reference point of the at least two discrete reference points corresponds to a center of the C-arm and a second reference point of the at least two discrete reference points lies on a line connecting an X-ray detector of the C-arm to an X-ray collimator of the C-arm and running through the center of the C-arm,
   wherein the trajectory for the medical robot system is planned dependent on a first reference vector, which points from the first reference point to the second reference point,
   wherein, dependent on the initial status, a second reference vector is calculated, which is perpendicular to a supporting plate of the patient couch, and/or a third reference vector is calculated, which is parallel to the supporting plate,
   wherein, for the planning of the trajectory, an alignment of the first reference vector is controlled or regulated in respect of the second reference vector and/or of the third reference vector, and wherein the planning of the trajectory is carried out in such a way that an angle between the second reference vector and a projection of the first reference vector is minimized in a plane perpendicular to the third reference vector, and/or an angle between the third reference vector and the projection of the first reference vector is minimized in a plane perpendicular to the second reference vector.

2. The method of claim 1, wherein the C-arm is mounted and/or guided in such a way that the C-arm is configured to be orbitally rotated about a first axis of rotation and rotated about a second axis of rotation perpendicular to the first axis of rotation, and
wherein the orbital rotation about the first axis of rotation and the rotation about the second axis of rotation correspond to mutually independent degrees of freedom of the plurality of degrees of freedom of the medical robot system.

3. An apparatus for data processing comprising:
at least one processor configured to:
determine an initial status of a medical robot system for each degree of freedom of a plurality of degrees of freedom of the medical robot system, wherein an initial value is obtained;
determine, based on the initial status, items of position information of at least two discrete reference points of a first component of the medical robot system in respect of one another;
determine, based on the initial status, further items of position information of at least two discrete further reference points of a second component of the medical robot system in respect of one another; and
plan a trajectory for the medical robot system dependent on the initial status, the items of position information, and the further items of position information; and
transfer the medical robot system from the initial status into a target status of the medical robot system along the trajectory,
wherein the medical robot system comprises a medical imaging modality that has the first component,
wherein the medical robot system comprises a patient couch that has the second component,
wherein the first component corresponds to a C-arm for X-ray-based imaging or is rigidly attached to the C-arm,
wherein a first reference point of the at least two discrete reference points corresponds to a center of the C-arm and a second reference point of the at least two discrete reference points lies on a line connecting an X-ray detector of the C-arm to an X-ray collimator of the C-arm and running through the center of the C-arm,
wherein the trajectory for the medical robot system is planned dependent on a first reference vector that points from the first reference point to the second reference point,
wherein, dependent on the initial status, a second reference vector is calculated, which is perpendicular to a supporting plate of the patient couch, and/or a third reference vector is calculated, which is parallel to the supporting plate,
wherein, for the planning of the trajectory, an alignment of the first reference vector is controlled or regulated in respect of the second reference vector and/or of the third reference vector, and wherein the planning of the trajectory is carried out in such a way that an angle between the second reference vector and a projection of the first reference vector is minimized in a plane perpendicular to the third reference vector, and/or an angle between the third reference vector and the projection of the first reference vector is minimized in a plane perpendicular to the second reference vector.

4. The apparatus of claim 3, wherein the C-arm is mounted and/or guided in such a way that the C-arm is configured to be orbitally rotated about a first axis of rotation and rotated about a second axis of rotation perpendicular to the first axis of rotation, and
wherein the orbital rotation about the first axis of rotation and the rotation about the second axis of rotation correspond to mutually independent degrees of freedom of the plurality of degrees of freedom of the medical robot system.

5. A robotic apparatus having a medical robot system, the robotic apparatus comprising:
an actuator system having a plurality of actuators, wherein the actuator system is configured to change a pose of a first component of the medical robot system independently of a pose of a second component of the medical robot system;
the medical robot system comprising a medical imaging modality that has the first component, wherein the medical robot system comprises a patient couch that has the second component, wherein the first component corresponds to a C-arm for X-ray-based imaging or is rigidly attached to the C-arm, and wherein a first reference point of at least two discrete reference points corresponds to a center of the C-arm and a second reference point of the at least two discrete reference points lies on a line connecting an X-ray detector of the C-arm to an X-ray collimator of the C-arm and running through the center of the C-arm, wherein the robotic apparatus is configured to measure an initial value for each degree of freedom of a plurality of degrees of freedom of the medical robot system; and
at least one processor configured to:
determine an initial status of the medical robot system for each degree of freedom of the plurality of degrees of freedom of the medical robot system, wherein the initial value for each degree of freedom is obtained;
determine, based on the initial status, items of position information of the at least two discrete reference points of the first component of the medical robot system in respect of one another;
determine, based on the initial status, further items of position information of at least two discrete further reference points of the second component of the medical robot system in respect of one another;
plan a trajectory for the medical robot system dependent on the initial status, the items of position information, and the further items of position information; and
transfer the medical robot system from the initial status into a target status of the medical robot system along the trajectory,
wherein the trajectory for the medical robot system is planned dependent on a first reference vector that points from the first reference point to the second reference point,
wherein, dependent on the initial status, a second reference vector is calculated, which is perpendicular to a supporting plate of the patient couch, and/or a third reference vector is calculated, which is parallel to the supporting plate, wherein, for the planning of the trajectory, an alignment of the first reference vector is controlled or regulated in respect of the second reference vector and/or of the third reference vector, and wherein the planning of the trajectory is carried out in such a way that an angle between the second reference vector and a projection of the first reference vector is minimized in a plane perpendicular to the third reference vector, and/or an angle between the third reference vector and the projection of the first reference vector is minimized in a plane perpendicular to the second reference vector.

6. The robotic apparatus of claim 5, wherein the C-arm is mounted and/or guided in such a way that the C-arm is configured to be orbitally rotated about a first axis of rotation and rotated about a second axis of rotation perpendicular to the first axis of rotation, and wherein the orbital rotation about the first axis of rotation and the rotation about the second axis of rotation correspond to mutually independent degrees of freedom of the plurality of degrees of freedom of the medical robot system.

* * * * *